(12) United States Patent
Klemm et al.

(10) Patent No.: US 12,214,100 B2
(45) Date of Patent: Feb. 4, 2025

(54) SHEET METAL HANDLE, AND COVER WITH SHEET METAL HANDLE

(71) Applicant: Aesculap AG, Tuttlingen (DE)

(72) Inventors: Svenja Klemm, Tuningen (DE); Matthias Henke, Fridingen (DE)

(73) Assignee: Aesculap AG, Tuttlingen (DE)

( * ) Notice: Subject to any disclaimer, the term of this patent is extended or adjusted under 35 U.S.C. 154(b) by 691 days.

(21) Appl. No.: 17/598,424

(22) PCT Filed: Mar. 27, 2020

(86) PCT No.: PCT/EP2020/058811
§ 371 (c)(1),
(2) Date: Sep. 27, 2021

(87) PCT Pub. No.: WO2020/193774
PCT Pub. Date: Oct. 1, 2020

(65) Prior Publication Data
US 2022/0175999 A1 Jun. 9, 2022

(30) Foreign Application Priority Data
Mar. 28, 2019 (DE) ...................... 10 2019 108 114.9

(51) Int. Cl.
*A45F 5/10* (2006.01)
*A61B 50/34* (2016.01)
(Continued)

(52) U.S. Cl.
CPC ................ *A61L 2/26* (2013.01); *A61B 50/34* (2016.02); *A61B 90/70* (2016.02);
(Continued)

(58) Field of Classification Search
CPC ..... A61L 2/26; A61B 90/70; A61B 2050/006; A61B 2050/3007; A61B 2050/3011;
(Continued)

(56) References Cited

U.S. PATENT DOCUMENTS 1,078,491 A * 11/1913 Field .................. B65D 25/2841
126/243
1,985,571 A * 12/1934 Hetzel ....................... A45F 5/10
294/158

(Continued)

FOREIGN PATENT DOCUMENTS

CN  101767675 A  7/2010
CN  107249541 A  10/2017
(Continued)

OTHER PUBLICATIONS

Written Opinion received in International Application No. PCT/EP2020/058811 dated Oct. 1, 2020, with translation, 13 pages.
(Continued)

*Primary Examiner* — Chuck Y Mah
(74) *Attorney, Agent, or Firm* — Christopher A. Rothe; CM Law

(57) ABSTRACT

A handle, preferably for a lid of a medical sieve basket, and a method of forming a handle. The handle includes a base body having a handle bar and at least one holding portion adjoining the handle bar, and at least one eyelet-shaped or bent fixing lug arranged at an end of the holding portion opposite the handle bar for pivotal mounting of the handle. The base body is formed of a planar sheet metal that includes at least one lug-like projection at the end of the holding portion opposite the handle bar. The projection is bent to form the fixing lug. The handle can be pivotally secured to a lid.

15 Claims, 3 Drawing Sheets

(51) Int. Cl.
*A61B 90/70* (2016.01)
*A61L 2/26* (2006.01)
*A61B 50/00* (2016.01)
*A61B 50/30* (2016.01)

(52) U.S. Cl.
CPC . *A61B 2050/006* (2016.02); *A61B 2050/3007* (2016.02); *A61B 2050/3011* (2016.02); *A61L 2202/121* (2013.01); *A61L 2202/123* (2013.01); *A61L 2202/17* (2013.01); *A61L 2202/24* (2013.01)

(58) Field of Classification Search
CPC ........ A61B 2202/121; A61B 2202/123; A61B 2202/17; A61B 2202/24
See application file for complete search history.

(56) References Cited

U.S. PATENT DOCUMENTS

| | | | | |
|---|---|---|---|---|
| 2,749,172 | A * | 6/1956 | Jacobs | A45F 5/1026 294/170 |
| 2,998,155 | A * | 8/1961 | Elskamp | B65D 25/282 217/125 |
| 3,191,830 | A * | 6/1965 | Goetz | A45F 5/12 294/156 |
| 3,548,906 | A * | 12/1970 | Murphy | B65D 33/06 383/905 |
| 4,482,181 | A * | 11/1984 | Shepherd | A47J 37/0786 294/12 |
| 5,659,440 | A * | 8/1997 | Acosta | G11B 23/0236 294/169 |
| 5,666,768 | A * | 9/1997 | Gavin | H02G 9/025 52/21 |
| 6,092,670 | A * | 7/2000 | Marriott | A47J 45/10 99/413 |
| 6,412,838 | B1 * | 7/2002 | Malamud | B65G 7/12 294/15 |
| 6,598,915 | B2 * | 7/2003 | Ngo | A47J 45/10 294/27.1 |
| 6,874,634 | B2 | 4/2005 | Riley | |
| 6,991,108 | B1 | 1/2006 | Rorato et al. | |
| 7,717,292 | B2 * | 5/2010 | Faust, III | A61B 50/30 16/421 |
| 7,854,340 | B1 | 12/2010 | Baker et al. | |
| 8,453,837 | B1 * | 6/2013 | Liu | H05K 5/023 220/759 |
| 9,643,543 | B1 * | 5/2017 | Race | B60R 9/065 |
| 2004/0144670 | A1 | 7/2004 | Riley | |
| 2006/0255217 | A1 * | 11/2006 | Wise | E06C 7/146 248/153 |
| 2008/0105641 | A1 | 5/2008 | Dobbelstein et al. | |
| 2010/0223759 | A1 * | 9/2010 | Baik | G06F 1/181 16/408 |
| 2017/0326015 | A1 | 11/2017 | Katzenstein | |
| 2019/0037802 | A1 * | 2/2019 | Woolworth | A01K 3/006 |
| 2019/0070480 | A1 * | 3/2019 | Armstrong | A45F 5/10 |

FOREIGN PATENT DOCUMENTS

| | | |
|---|---|---|
| DE | 20105328 U1 | 7/2001 |
| DE | 102016121723 B3 | 11/2017 |
| EP | 3321205 A1 | 5/2018 |
| EP | 3434611 A2 | 1/2019 |
| FR | 2737105 A1 | 1/1997 |
| FR | 2779701 A1 * 12/1999 | ........... A45F 5/1026 |
| GB | 2103182 A | 2/1983 |
| WO | 0178619 A1 | 10/2001 |

OTHER PUBLICATIONS

Search Report received in German Application No. 10 2019 108 114.9 dated Feb. 11, 2020, with translation, 10 pages.
Search Report received in International Application No. PCT/EP2020/058811 dated Jul. 14, 2020, with translation, 6 pages.
Office Action received in Chinese Application No. 202080018931.8 dated May 7, 2022, with translation, 18 pages.
Search Report received in Chinese Application No. 202080018931.8 dated Apr. 28, 2022, with translation, 6 pages.

* cited by examiner

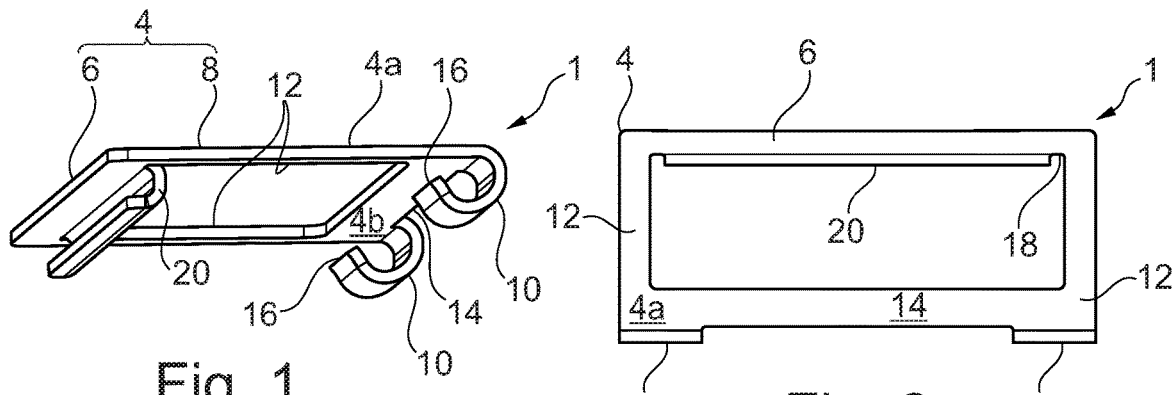
Fig. 1
Fig. 2
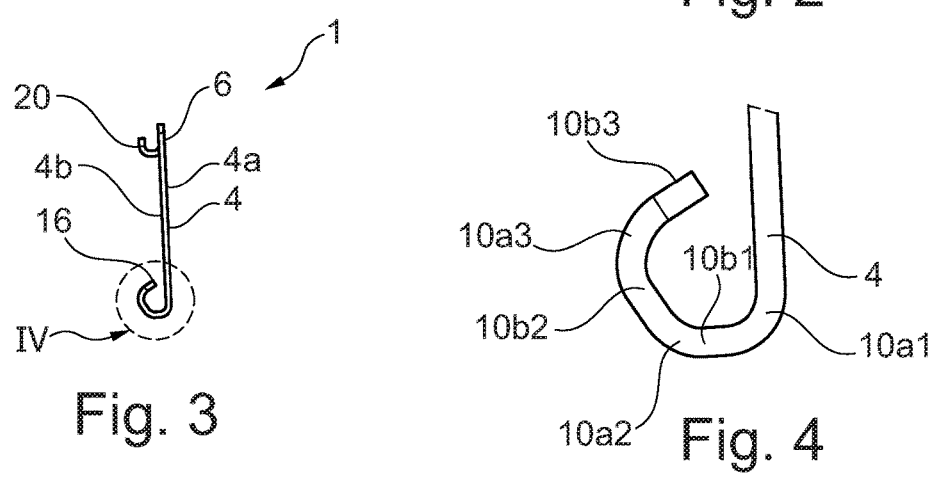
Fig. 3
Fig. 4
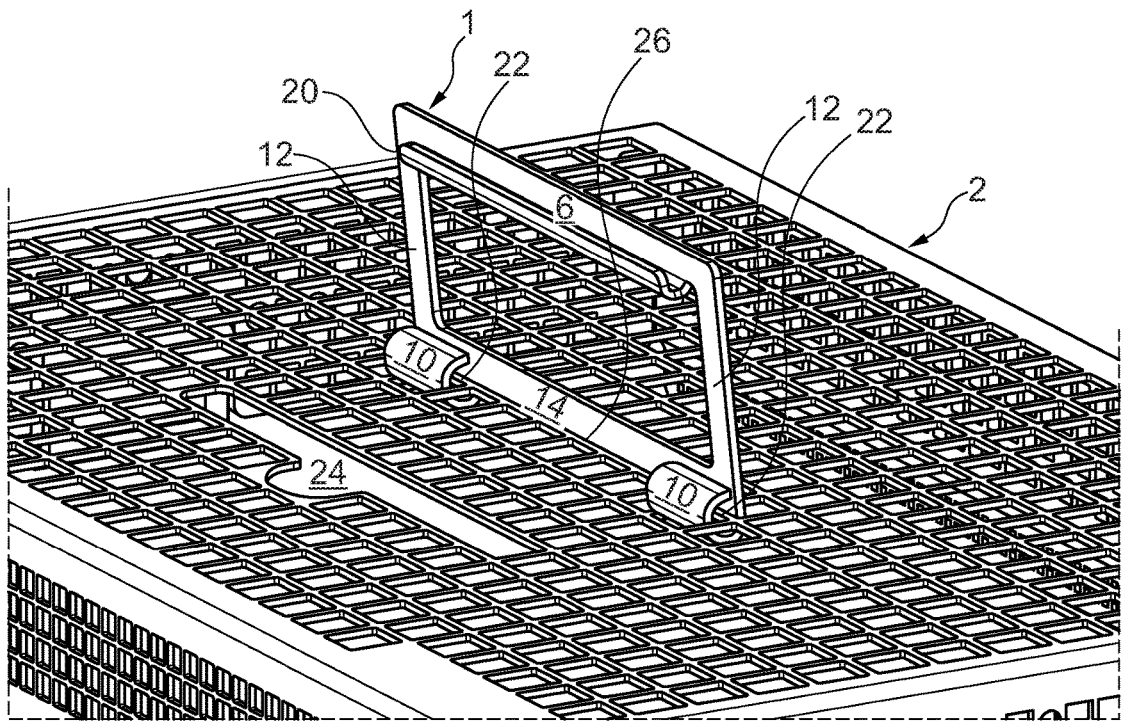
Fig. 5

SHEET METAL HANDLE, AND COVER WITH SHEET METAL HANDLE

CROSS-REFERENCES TO RELATED APPLICATIONS

This application is the United States national phase entry of International Application No. PCT/EP2020/058811, filed Mar. 27, 2020, and claims the benefit of priority of German Application No. 10 2019 108 114.9, filed Mar. 28, 2019. The contents of International Application No. PCT/EP2020/058811 and German Application No. 10 2019 108 114.9 are incorporated by reference herein in their entireties.

FIELD

The present invention relates to a handle for/of a preferably grid-like constructed lid, in particular a lid for a washing container/sieve basket for medical washing items/packaged items, a lid with said handle, and a method for forming said handle from a sheet metal on said lid.

By definition, a handle is understood to be a bracket-shaped loop construction having a bar-shaped or rod-shaped handrail (handle bar), at the opposite ends of which a respective holding leg extends, preferably at right angles to the handrail, and at the free ends of which at least one connecting structure, for example in the form of hinge pins, suspension eyelets or loops, is arranged/formed. The handrail length as well as the length of the holding legs is functionally dimensioned in such a way that the handrail can be grasped around its full circumference with a human hand in a portion between the holding legs (aligned parallel to each other) in any pivot position of the handle.

BACKGROUND

For cleaning or washing medical instruments, for example surgical forceps or clamps, so-called 'wash trays' or washing baskets/sieve baskets/sterilizing sieve trays are used, which have a receptacle or receptacle container for the washing items or packaged items, respectively, and a lid for closing these sieve baskets/washing baskets.

For optimum rinsing of the washing items, the receptacles and lids of the wash baskets are grid-like or, respectively, consist of a grid structure. In addition, a respective handle is provided on the lids of the wash baskets, with which the wash basket can be lowered into a sterile container, for example, and can be lifted out of it again.

Wash baskets are known from the prior art which are formed from a grid structure and which have a receptacle for medical washing items and a lid for closing the sieve baskets/wash baskets/sterilization sieve trays. The lids usually have a substantially planar upper side on which a carrying handle is arranged. Regardless of the single or multiple use of a container, the carrying handle on the lid of the wash baskets also has to be taken into account when dimensioning the interior of the container and/or the wash basket or wash baskets, since this requires additional space inside the container due to its own height.

Since additional space is associated with higher material requirements in the construction of the container (container height), it is important to utilize the container interior as fully as possible and in particular to reduce unused space between the upper lid side of the wash basket lid and the lower lid side of the container lid or, respectively, between the upper lid side of a lower wash basket and the bottom of a wash basket stacked above it.

This problem is already known from the prior art and is limited by attaching drop handles to the upper lid side instead of fixed handles. These drop handles according to the definition given at the beginning are usually made of a round material, for example a metal rod of round cross-section. The round material is then formed into a handle in the shape of a bent round bar by angulating or, respectively, bending the two ends of the round material and orienting them coaxially (in parallel) to each other by bending the round material located between the two ends.

The handle, which is shaped in the shape of a bent round rod, is then connected to the lid of the wash basket by rolling up the lid sheet metal to form a handle suspension which grips the angled ends of the handle. Within the handle suspension, the handle can then be rotated like a hinge and can be pivoted relative to the upper lid side so that the handle can assume an upright position when transporting the lid or, respectively, the wash basket and can be pivoted or folded flat onto the lid when closing the container lid over the wash basket placed inside the container and/or when stacking several wash baskets on top of each other.

Nevertheless, the lid sheet metal rolled up to form a suspension, which has to enclose the angled ends of the bent round rod on the circumference, builds up a total height of more than 5 mm on the upper lid side, so that when the container lid is closed over the wash basket and/or when the wash baskets are stacked one on top of the other, a slit of more than 5 mm remains between the upper lid side of the wash basket and the container lid or, respectively, base of the wash basket arranged above it. The problem of insufficient utilization of space in the container is therefore only inadequately reduced.

SUMMARY

The object of the present invention is thus to overcome or at least reduce the disadvantages of the prior art and, in particular, to create a (manual) handle according to the definition given at the beginning or, respectively, a lid with a (manual) handle for a medical sieve basket, which makes it possible to utilize the interior space of a container as completely as possible when filling it with at least one sieve basket and/or to reduce the clearance between the upper lid side of a lower sieve basket and the bottom of a sieve basket arranged above it when stacking several sieve baskets one on top of the other. In particular, the usable interior space of the sieve basket is not to be impaired or is to be impaired only slightly. In addition, the handle should preferably be easy to manufacture and to mount on the lid. Furthermore, missed washing areas in particular are preferably to be prevented, and a possibility is to be provided for the handle to automatically assume a space-saving position.

A basic idea of the invention is to create a (manual) handle, which is as flat as possible, for/of a lid for/of a sieve basket/wash basket, wherein the handle's mounting structure on the lid results in no or only a slight increase in height. When the handle is mounted on the lid, it should be able to assume a position in which the mounted handle builds up as little height as possible on the upper lid side, in particular without or only to a small extent reducing the usable interior space in the wash basket, by partially recessing the handle into the lid. It is also intended to be possible to produce the handle by forming a (cut-to-size) sheet metal or, respectively, sheet-metal blank and to mount it on the lid.

More precisely, the (manual lid) handle for/of a medical sieve basket according to the invention consists of a thin-walled sheet (sheet metal) made (punched out/cut out) into a basic profile/base body comprising or consisting of an (upper) handle bar with a holding portion adjoining the same, the holding portion preferably having two holding arms/holding legs which adjoin the handle bar (at right angles) on both sides thereof and the free arm ends of which are at least partially bent to form bearing eyelets/fixing lugs, or, respectively, on the free arm ends of which bearing eyelets/fixing lugs are arranged, and optionally having a (middle or lower) stiffening bar in the region between the handle bar and the bearing eyelets or directly adjacent to the bearing eyelets, which connects the two holding arms/holding legs in a stiffening manner (as one piece of material).

This construction allows the handle bar, the holding arm and the bearing eyelets/fixing lugs to be made of the same (thin-walled) sheet-metal material, preferably in one piece, wherein the stiffening bar (extending essentially parallel to the handle bar), which is also made of the same (thin-walled) sheet-metal material, preferably in one piece with the holding arms, provides the necessary bending/twisting stiffness of the (manual) handle.

Preferably, a (handle) trough/handle lug is bent at an inner edge portion of the handle bar, which prevents that a sharp handle edge resulting from the thin-walled sheet-metal material cuts into a human hand when grasping the handle bar around its full circumference.

Further preferably, the bending direction of all bent portions of the (manual) handle is the same, so that all bends in the same direction can preferably be made in a single bending step (without turning over the sheet-metal blank).

In other words, a (manual) handle is provided for a preferably grid-like constructed container lid, the basic shape of which consists of or, respectively, is made of a correspondingly cut sheet, for example in the form of a (substantially) rectangular closed ring. Thereby, the handle has a substantially planar (unbent) base body (made of the thin-walled sheet-metal material), which has/forms (in one piece) at least one lug-shaped projection at or, respectively, of a first outer edge, the projection being bent into a fixing lug/eyelet, which is provided and adapted to pivotably secure the (manual) handle to a lid, preferably by (at least partially) gripping/enclosing a mandrel-shaped or rod-shaped part of the lid. Thus, the at least one bent fixing lug forms a pivot hinge by enclosing a part of the lid over its width, at which the handle can be deflected relative to the lid.

In particular, the at least one fixing lug is bent around a fixing strut on the lid and forms (in the assembled state) a (narrow) slit between itself and the holding portion/holding leg, or the free end of the respective bent lug lies directly against the holding portion/holding leg in an abutting manner.

Specifically, a (manual) handle preferably for/of a lid for/of a medical sieve basket is provided, comprising a base body (made of a thin-walled sheet-metal material) having or consisting of a handle bar and a holding portion (also made of the thin-walled sheet-metal material) adjoining or, respectively, connected to the handle bar (in one piece of material), and at least one eyelet-shaped or bent fixing lug (also made of the thin-walled sheet-metal material), which is arranged (one-piece of material) at an end of the holding portion opposite the handle bar for pivot mounting of the handle. For this purpose, the base body of the handle is formed from a (substantially) planar sheet metal (unbent and/or cut to size) which, at the end of the holding portion opposite the handle bar, is made into at least one lug-like projection extending the holding portion, the projection being bent to form the fixing lug.

In particular, the fixing lug is bent with respect to the holding portion or, respectively, base body such that its free end is oriented towards a lower side of the holding portion or, respectively, base body. Preferably, the upper side of the handle is a planar bearing surface that is (substantially) plane-parallel to the lower side of the base body, and the fixing lug does not extend beyond the bearing surface in a direction perpendicular to the bearing surface.

In summary, the handle is thus an initially unbent (thin-walled) sheet-metal part which is cut into an intended, (substantially rectangular) annular basic shape consisting of the handle bar, the two-legged holding portion and the at least one lug projecting from the holding portion, wherein the projecting lug is bent in relation to the holding portion (to form an eyelet). The remaining part of the basic shape (handle bar and holding portion) initially remain unbent. This results in the described planar, unbent base body typical of a sheet metal, which has the bent fixing lug at one end thereof for pivot mounting of the handle.

Advantages are achieved at least in that the (manual) handle in a rest position or, respectively, contact position on the lid, in which the handle rests with the lower side of its base body on the lid, only builds up height in the form of its own sheet thickness on the lid (in particular because the fixing lug is bent in the direction of the lower side of the handle and thus projects into the lid in the rest position defined above). Furthermore, the planar base body resting on the lid causes no or, respectively, only negligible missed washing areas, which allows better cleaning.

The sheet metal is in particular a sheet metal of (substantially) constant wall thickness, preferably of 1.25 mm. In this way, sufficiently high (torsional) stability can be achieved with the lowest possible sheet-metal thickness and consequently the lowest possible build-up in height.

Preferably, the holding portion has or consists of two holding legs, which are arranged at the free ends of the handle bar and at the free ends/end portions of which a respective fixing lug is arranged/formed. In particular, a respective holding leg adjoins the free ends of the handle bar, preferably substantially perpendicularly thereto.

In particular, the holding legs may be shaped mirror-inverted to each other and/or I-shaped or L-shaped.

In this way, the load/traction force applied to the handle when the wash basket connected to the lid is carried is advantageously distributed evenly over the handle.

In particular, the holding portion further has a stiffening bar which connects the two holding legs between the handle bar and the fixing lug, preferably in the area of the free ends of the holding legs, in one piece. Particularly preferably, the stiffening bar is directly adjacent to the fixing lugs.

In this way, the stability and strength of the handle is further improved. For the sake of clarity, it should be noted at this point that the stiffening bar is also part (one piece of material) of the planar sheet metal and is unbent.

Particularly preferably, at least one channel-shaped or trough-shaped gripping lug is formed on an inner edge portion of the handle bar. For this purpose, a sheet-metal band, which widens the handle bar in the direction of the at least one lug-like projection, may be formed and bent at the inner edge portion.

In this way, an easily constructed, particularly comfortable gripping portion is formed.

The inner edge is to be understood as the edge of the handle bar facing the at least one fixing lug. Furthermore, for clarification purposes, it is noted here that the gripping lug is part of the sheet-metal body from which the handle is made, and the gripping lug is thus connected in one piece to the handle bar with respect to which it is bent. Like the at least one fixing lug, the bent gripping lug does not project beyond the upper side of the handle in the direction perpendicular thereto.

Another aspect of the present invention relates to the configuration of the fixing lug or, respectively, eyelet.

Accordingly, the handle according to the invention has a base body made of a (thin-walled) sheet metal, which is composed of a handle bar and two holding legs, which extend at the ends of the handle bar at a substantially right angle thereto and are bent at their free ends to form the fixing lugs/eyelets. Optionally, a stiffening bar is formed between the holding legs (close to the fixing lugs) in one piece with the holding legs, which extends substantially parallel to the handle bar and connects the two holding legs to each other in the area of their free ends.

The fixing lugs, which are bent from the planar sheet metal and in extension of the holding legs, have the following longitudinal portions in the indicated order starting from the respective holding leg:
 a first bent portion that bends the fixing lug starting from the holding leg by a first obtuse angle preferably between 90° and 110° to the holding leg,
 a first straight portion of a first length adjoining (adjacent to) the first bent portion,
 a second bent portion that bends the first straight portion by a second obtuse angle in the same bending direction as the first bent portion, wherein the second obtuse angle is greater than the first obtuse angle, preferably between 120° and 150°,
 a second straight portion adjoining the second bent portion and having a second length greater than the first length,
 a third bent portion that bends the second straight portion by a third obtuse angle in the same bending direction as the second bent portion, wherein the third obtuse angle substantially corresponds to the first obtuse angle, but the curvature radius of the third bent portion is greater than the curvature radius of the first bent portion, and
 a third straight portion adjoining the third bent portion and having a third length substantially corresponding to the first length.

In particular in the case of a pivot pin also made of a planar, thin-walled sheet metal, this shaping allows the width (not metal sheet wall thickness) of the pivot pin to be adjusted to the inner dimensions of the eyelet formed in such a way that the eyelet can be rotated around the (lug-shaped) pivot pin up to a certain pivot angle, at which the pivot pin wedges into the eyelet and thus prevents further pivoting. Depending on the direction of rotation of the (lug-shaped) pivot pin, the wedging angle corresponds to the maximum set-up angle/tilt-up angle of the (manual) handle with respect to the lid to which the (manual) handle is hinged.

According to the invention, a lid for/of a container is further provided, in particular for/of a medical sieve basket, with a handle as described above. The lid further comprises at least one fixing strut or at least one hinge pin, which is gripped/enclosed by the at least one fixing lug circumferentially (along the circumference of the fixing strut in sections or completely) and to which the handle is pivotably attached.

In a grid-like lid, the fixing strut may be part of the lid-grid structure. If the handle does not completely enclose the circumferential side of the fixing strut, the opening of the fixing lug or, respectively, of the slit between the free end of the fixing lug and the holding portion (or, respectively, base body) is dimensioned such in the assembled state of the handle that the fixing strut cannot be removed through the opening.

In this lid-handle design, the handle may advantageously lie flat against the lid and builds up no more height than its own sheet-metal thickness, in particular the sheet-metal thickness of its planar base body, on the lid.

In particular, the at least one fixing lug is positioned in a rest position of the handle, in which it rests with its base body against the lid, on the side of the handle facing the lid, which is to be understood as the lower side of the handle.

Advantageously, the height of the bent fixing lug is therefore not added to the lid.

In particular, the lid further comprises a recess or trough positioned and provided and adapted such that the gripping lug is (fully) recessed into the recess or trough in the rest position of the handle.

Further preferably, the lid side facing the handle in the rest position of the handle is an upper lid side and the fixing strut does not project beyond the (remaining) upper lid side. In particular, the fixing strut is flush with the (remaining) upper lid side.

This enables the base body of the handle to rest on the lid (almost) without gaps/clearances.

Furthermore preferably, the deflection/pivot of the handle relative to the lid is limited to a maximum deflection angle/pivot angle of 80° to 89°, particularly preferably 85°. This can be achieved, for example, by an outer edge of the holding portion coming into contact with the lid (upper lid side) at a deflection angle/pivot angle of 80° to 89°, in particular 85°, which causes the handle to abut the lid at this angle and limits the deflection to a maximum.

Specifically, the relative position between the lower edge of the holding portion facing the lid, in particular of the stiffening bar, and of the at least one fixing lug/pivot lug is preferably determined in such a way that, when the maximum deflection angle is reached, the lower edge abuts on the upper lid side.

This ensures that the handle cannot be deflected up to a vertical position relative to the upper lid side and that the handle consequently returns to its rest position when an external force that deflects the handle is removed. This prevents the handle from interfering with the stacking of another wash basket or the closing of the container with a container lid when it is no longer needed for carrying the wash basket.

The invention further relates to a method for forming a handle as described above on a lid as described above from a (planar, cut to size) sheet metal or, respectively, sheet-metal blank, which has a base body consisting of a handle bar and at least one holding portion adjoining the latter and at least one lug-like projection extending the holding portion and having a free end facing away from the holding portion, comprising the steps of:
 (machine) forming the at least one lug-like projection into a curved fixing lug such that it assumes an open, bent shape;
 inserting the fixing strut into the open, bent fixing lug so that it openly encloses the fixing strut; and
 (machine) forming the open fixing lug in such a way that the free end of the fixing lug is arranged closer to the base body and/or the free end comes to rest on the base body and the fixing strut is (almost completely) enclosed and pivotably secured by the fixing lug.

Preferably, at an inner edge of the handle bar, the sheet-metal blank is formed into at least one sheet-metal band widening the sheet-metal blank towards the lug-like projection, and the method further comprises the step of (machine) forming the sheet-metal band so that it forms a bent gripping lug.

In this way, the handle described above can be manufactured from a single component (sheet metal) and the lid with handle described above can be realized by simple method steps.

BRIEF DESCRIPTION OF THE DRAWING FIGURES

The invention is described in more detail below with reference to the accompanying drawing figures and by way of preferred configuration examples. The following is shown:

FIG. 1 shows a perspective view of a handle in an embodiment according to the invention;

FIG. 2 shows a top view of the handle in the embodiment according to the invention;

FIG. 3 shows a side view of the handle shown in FIG. 2 in the embodiment according to the invention;

FIG. 4 shows an enlarged view of the area IV of FIG. 3;

FIG. 5 shows a perspective view of a lid in an embodiment according to the invention in a deflected position of the handle;

FIG. 7b shows an enlarged view of the area VIIb of FIG. 7a;

FIG. 8b shows an enlarged view of the area VIIIb of FIG. 8a;

The figures are merely schematic in nature and are intended solely for the purpose of understanding the invention. Identical elements are designated by the same reference signs.

DETAILED DESCRIPTION

Figure 6:
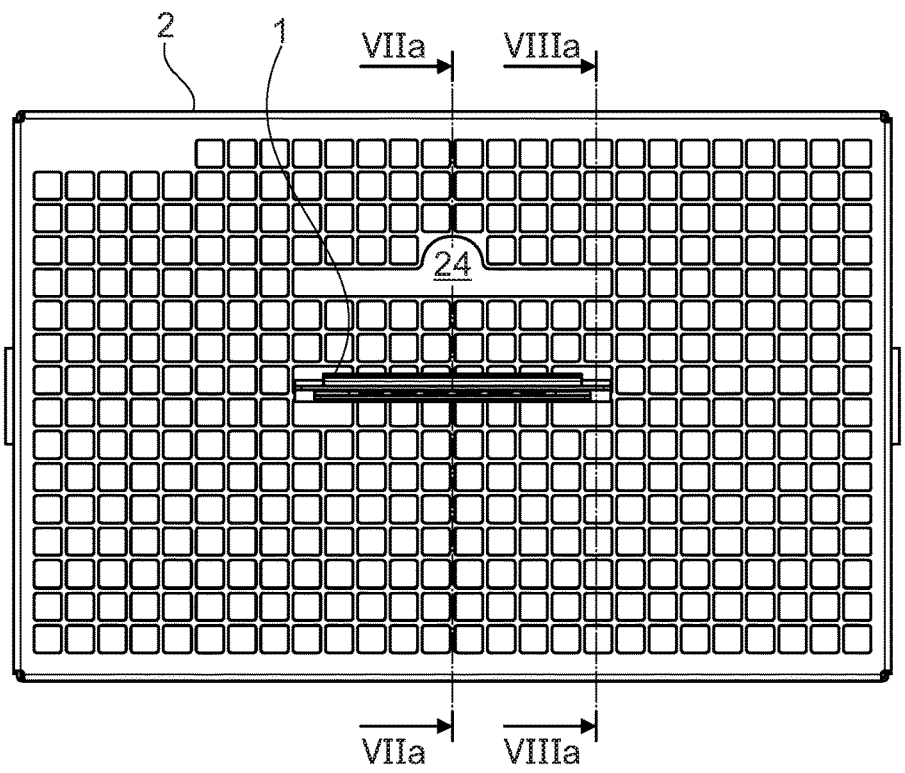
FIG. 6 shows a top view of the lid in the deflected position of the handle shown in FIG. 5.

FIG. 1 shows a perspective view of a handle 1 in an embodiment according to the invention. The handle 1 is provided for a lid 2 (see FIG. 5) of a medical sieve basket and consists of a base body 4, which has a handle bar 6 and a holding portion 8 adjoining the handle bar, and two eyelet-shaped or curved fixing lugs 10, which are arranged at an end of the holding portion 8 opposite the handle bar 6 for pivot mounting of the handle 1. The base body 4 of the handle 1 consists of a planar sheet metal, which, at the end of the holding portion 8 opposite the handle bar 6, is made into two lug-like projections extending the holding portion 8, which are bent to form the fixing lugs 10. The holding portion 8 has two holding legs 12, each of which has a respective fixing lug 10 at its free end. The holding legs 12 are each connected at right angles to a respective free end of the handle bar 6. A stiffening bar 14 is located between the holding legs 12, which connects the two holding legs 12 and is directly adjacent to the fixing lugs 10.

The substantially rectangular-shaped, planar base body 4 has a planar upper side 4a and a lower side 4b extending plane-parallel to the upper side 4a. The bent fixing lugs 10 initially extend substantially perpendicular to the lower side 4b and in their further course assume a convexly bent shape with respect to the lower side 4b, so that a free end 16 of the fixing lugs 10 faces the lower side 4b.

At an inner edge 18 (shown in FIG. 2) of the handle bar 6, a bent gripping lug 20 is provided which also initially extends substantially perpendicularly to the lower side 4b and in its further course becomes oriented substantially parallel to the lower side 4b so that the gripping lug 20 forms a groove or trough. The gripping lug 20 and the handle bar 6 together form the gripping portion at which a user grips (around) the handle to carry the lid or, respectively, the container closed with the lid.

The shown shape of the handle 1 corresponds to a semi-finished product of the handle 1 before it is connected to a lid 2. In the semi-finished product, the free ends 16 of the fixing lugs 10 are clearly spaced from the lower side 4b.

FIG. 2 is a top view of the handle 1 in the embodiment according to the invention. The base body 4 can be seen from its upper side 4a. The two fixing lugs 10 are arranged on the holding legs 12 in such a way that their outer edges are flush with the outer edges of the holding legs 12. It can further be seen that the stiffening bar 14 is directly adjacent to the fixing lugs 10. The gripping lug 20 extends along a portion of the inner edge 18 and is arranged centrally thereon.

FIG. 3 shows a side view of the handle shown in FIG. 2 in the embodiment according to the invention. In particular, the plane-parallel course of the upper side 4a and the lower side 4b of the base body 4, the distance of the free end 16 of the fixing lug 10 from the lower side 4b and the gripping lug 20, which together with the handle bar 6 forms the gripping portion of the handle 1, can be seen.

FIG. 4 shows an enlarged view of the area IV of FIG. 3. As can be seen from FIG. 4, the course of the bent fixing lug 10 has bent portions $10a1$, $10a2$, $10a3$ as well as linear portions $10b1$, $10b2$, $10b3$. The bent portions $10a1$-3 and the linear portions $10b1$-3 are arranged alternately. The curvature radii of the bent portions $10a1$-3 may be the same or different. In particular, the curvature radius of the bent portion $10a1$ adjacent to the base body 4 may be smaller than the remaining two bent portions $10a2,3$ which have the same curvature radius.

FIG. 5 shows a perspective view of a lid 2 with a handle 1 in an embodiment according to the invention. The handle 1 is in a deflected position. The handle 1 can be seen from its lower side 4b. The lid 2 is formed in the form of a grid structure. It can be seen that the handle 1 is attached/mounted to the lid 2 with its fixing lugs 10, in that the fixing lugs 10 each grip/enclose a fixing strut 22 integrated into the grid structure of the lid 2. The free ends 16 of the fixing lugs 10 rest against the lower side 4b. In this way, the fixing lugs 10 each form a hinge and the fixing struts 22 each form a hinge pin, whereby the handle 1 is held pivotably on the lid 2. In the position shown, the handle 1 is in a maximum deflected position relative to the upper lid side. In the illustrated maximum deflected position of the handle 1, an outer edge 26 of the stiffening bar 14, or more precisely the outer edge of the stiffening bar 14 on the lower side 4b, comes into contact with the lid 2/upper lid side and thereby limits the pivot angle or deflection angle. The maximum pivot angle or deflection angle is 85°. A recess 24 in the lid 2 can also be seen. The recess 24 is positioned and dimensioned on the lid 2 in such a way that the gripping lug 20 can enter the recess 24 and be received in it when the handle 1 is pivoted back into its rest position (see FIGS. 9 and 10).

FIG. 6 shows a top view of the lid 2 in the deflected position of the handle 1 shown in FIG. 5.

Figure 7A:
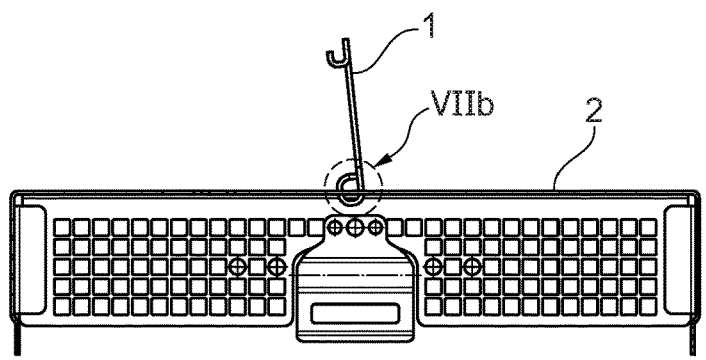
FIG. 7a shows a sectional view of the lid and handle in the embodiment according to the invention along the line VIIa of FIG. 6.

FIG. 7a shows a sectional view of the lid 2 with mounted handle 1 along line VIIa of FIG. 6. The handle 1 is deflected to the maximum relative to the lid 2.

Figure 7B:
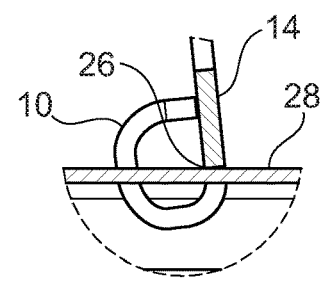

FIG. 7b shows an enlarged view of the area VIIb of FIG. 7a. It can be seen that the outer edge 26 of the stiffening bar 14 limits the pivot angle of the handle 1 relative to the lid 2 by coming into contact with a grid strut 28 of the lid 2. The grid strut 28 shown thus forms a stop for limiting the pivot angle. Since the maximum pivot angle is 85°, the handle 1 falls back into its rest position due to gravity after the external force that deflects the handle 1 from its rest position is removed.

Figure 8A:
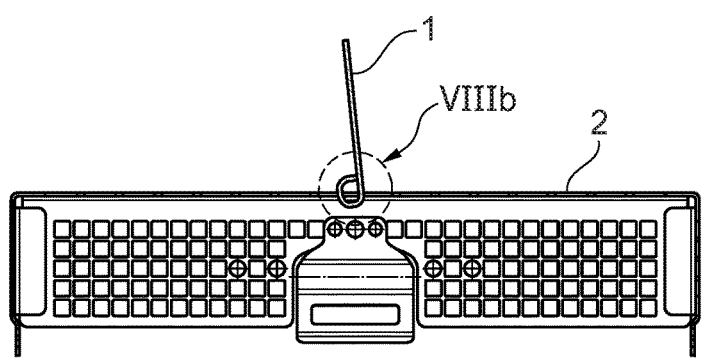
FIG. 8a shows a sectional view of the lid and handle in the embodiment according to the invention along the line VIIIa of FIG. 6.

FIG. 8a shows a sectional view of the lid 2 with mounted handle 1 along the line VIIIa of FIG. 6.

Figure 8B:
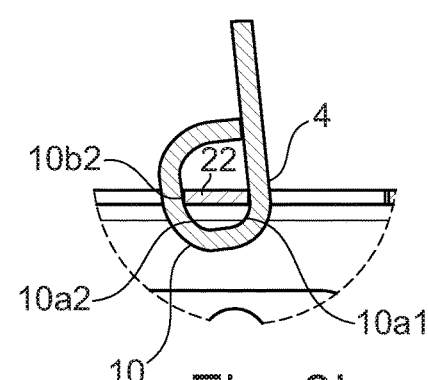

FIG. 8b shows an enlarged view of the area VIIIb of FIG. 8a, which shows the handle 1 in the same deflected position as in FIG. 7b, thus in exactly the position in which the outer edge 26 of the handle bar 14 comes into contact with the lid 2. In this position, the handle 1 cannot be moved further away from the upper lid side in a direction (substantially) perpendicular to the upper lid side. This is realized, for example, by the fact that in the relative position of fixing lug 10 and fixing strut 22 shown, the inner diameter of the fixing lug 10 below the fixing strut 22 is equal to or smaller than the width of fixing strut 22. The width of the fixing strut 22 means its extension along the upper lid side in a direction from the fixing lugs 10 towards the recess 24. Below the fixing strut 22 means in this context a direction away from the upper lid side.

Figure 9:
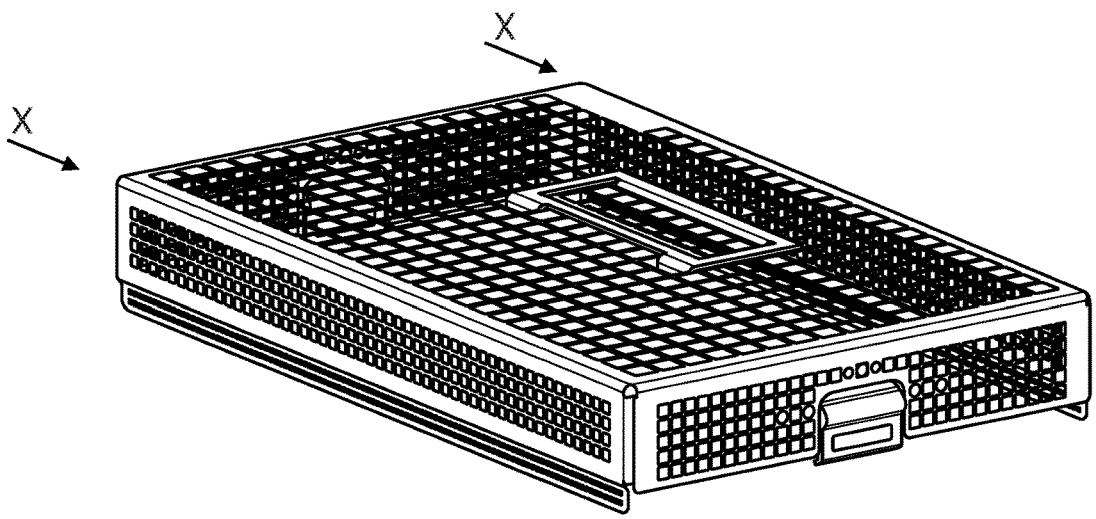
FIG. 9 shows a perspective top view of the lid in the embodiment according to the invention in the rest position of the handle.

FIG. 9 shows a perspective top view of the lid 2 in the rest position of the handle 1, in which the handle 1 rests (substantially) without gaps on the lid 2 and the fixing lugs 10 and the gripping lug 20 are recessed into the lid 2. This can be seen in particular with regard to FIG. 10.

Figure 10:
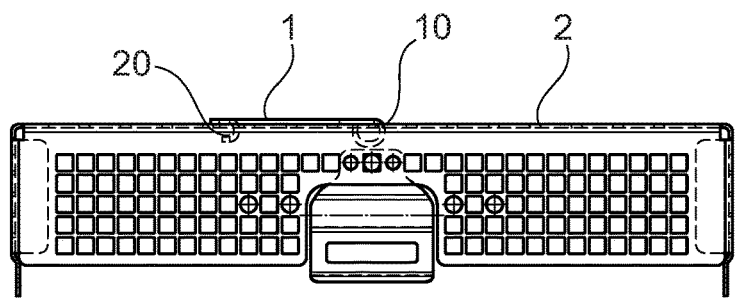
FIG. 10 shows a side view of the lid shown in FIG. 9 in the embodiment according to the invention.

FIG. 10 shows a side view of the lid 2 shown in FIG. 9 in the embodiment according to the invention in a rest position of the handle 1. It can be seen that the handle 1 or, respectively, the base body 4 of the handle 1 rests with its lower side 4b (substantially) without gaps on the lid 2 (see also FIG. 11), and that the total height of the handle 1 which it builds up on the lid 2 is no more than the thickness of the sheet metal from which the handle 1 is made. In this position, the fixing lugs 10 and the gripping lug 20 are recessed into the lid 2 or, respectively, reach through it.

Figure 11:
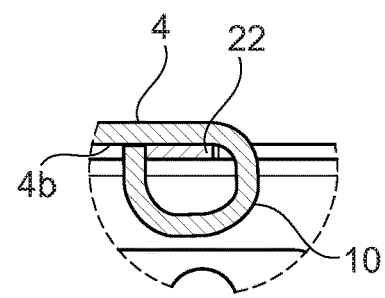
FIG. 11 shows a sectional view of the handle in the embodiment according to the invention in the region of a fixing lug in the rest position of the handle.

FIG. 11 shows a sectional view of the handle 1 in the embodiment according to the invention in the region of a fixing lug 10 in the rest position of the handle 1. In the rest position, the base body 4 rests with the lower side 4b against the lid 2 and the fixing lug 10 encloses the fixing strut 22. In this case, the base body 4 also rests on the fixing strut 22, which forms part of the upper lid side.

Figure 12:
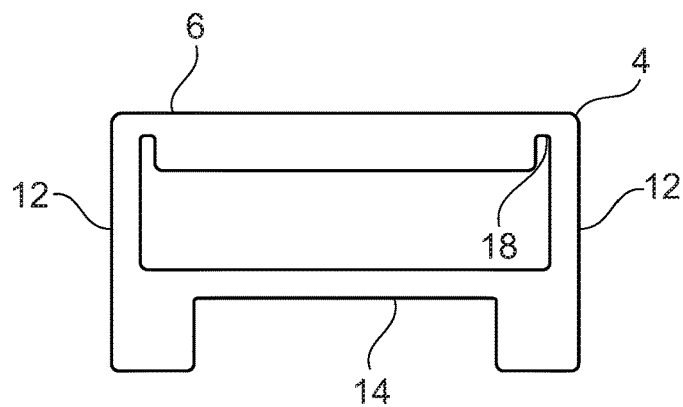
FIG. 12 shows a top view of a sheet metal from which the handle of the embodiment according to the invention is made.

FIG. 12 shows a top view of a cut (to size) sheet metal or, respectively, a sheet-metal blank from which the handle 1 is manufactured. The handle 1 is manufactured by (machine) forming the shown sheet-metal blank. The sheet-metal blank has the base body 4 with the handle bar 6, the two holding legs 12 and the stiffening bar 14 as well as two lug-like projections, each of which is arranged at the end of the holding legs 12 facing away from the handle bar 6. A sheet-metal band is formed on the handle bar 6 at an inner edge portion 18, said sheet-metal band widening the handle bar 6 toward the lug-like projections. The shape of the sheet-metal blank shown may be formed by punching (out) an ordinary sheet metal.

For forming the handle 1 from the sheet-metal blank shown, the lug-like projections are formed by forming, for example bending, into the open bent shape shown in FIG. 4 and each form a fixing lug 10. The sheet-metal band is also formed by forming, for example bending, into the shape shown in FIG. 3 and forms the gripping lug 20. The sheet metal now has the shape of the semi-finished item of the handle 1 in which the handle 1 can be mounted on the lid 2.

For mounting the semi-finished handle 1 with the lid 2, the fixing lugs 10 are guided around the fixing struts 22 of the lid 2 or, respectively, the fixing struts 22 are guided through the slit between the free ends 16 and the lower side 4b. The fixing lugs 10 are then pressed further towards the lower side 4b and formed so that the free ends 16 come to rest on the lower side 4b and the fixing lugs 10 are closed. The handle 1 is now pivotably secured to the lid 2.

It is noted for the sake of clarity that the entire handle, including the base body and all lugs, is manufactured in one piece from one metal sheet.

The invention claimed is:

1. A handle for a lid of a medical sieve basket, the handle comprising:
    a base body having or forming a handle bar and a holding portion adjoining the handle bar; and
    at least one fixing lug that is eyelet-shaped or bent in a rounded shape and is arranged at an end of the holding portion opposite the handle bar for pivotal mounting of the handle,
    the base body comprising a planar sheet metal, which, at the end of the holding portion opposite the handle bar, is made as one piece into at least one lug-like projection extending the holding portion in a direction opposite the handle bar, the at least one lug-like projection being bent round with respect to the holding portion to form the at least one fixing lug such that the at least one fixing lug is configured over its width for pivotal mounting of the handle.

2. The handle according to claim 1, wherein:
    the holding portion comprises a first holding leg and a second holding leg,
    the at least one fixing lug comprises a first fixing lug at a free end/end portion of the first holding leg and a second fixing lug at a free end/end portion of the second holding leg,
    the first holding leg and the second holding leg each adjoining a free end of the handle bar,
    a length of the handle bar between the first holding leg and the second holding leg, and lengths of the first holding leg and the second holding leg are dimensioned for gripping the handle bar around its full circumference with a human hand in any pivot position of the handle.

3. The handle according to claim 2, wherein the holding portion further comprises a stiffening bar which connects the first holding leg and the second holding leg in one piece of material between the handle bar and the at least one fixing lug.

4. The handle according to claim 3, wherein a position of the stiffening bar relative to the at least one fixing lug and/or a shape of the stiffening bar is determined in such a way that the stiffening bar additionally forms a pivot stop of the handle, which is provided and designed to come into pivot stop contact upon reaching a pivoted-out position of the handle.

5. The handle according to claim 1, wherein the at least one fixing lug has the following longitudinal portions in order starting from the respective holding legs:
   a first bent portion that bends the at least one fixing lug starting from the first holding leg by a first obtuse angle to the holding legs;
   a first straight portion of a first length adjoining the first bent portion;
   a second bent portion that bends the first straight portion by a second obtuse angle in a same bending direction as the first bent portion, wherein the second obtuse angle is greater than the first obtuse angle;
   a second straight portion adjoining the second bent portion and having a second length greater than the first length;
   a third bent portion that bends the second straight portion by a third obtuse angle in the same bending direction as the second bent portion, wherein the third obtuse angle substantially corresponds to the first obtuse angle, but a curvature radius of the third bent portion is greater than a curvature radius of the first bent portion; and
   a third straight portion adjoining the third bent portion and having a third length substantially corresponding to the first length.

6. The handle according to claim 1, wherein at least one channel-shaped or trough-shaped gripping lug is formed on an inner edge portion of the handle bar.

7. The handle according to claim 6, wherein a sheet-metal band widening the handle bar towards the at least one lug-like projection is formed and bent to form the at least one channel-shaped or trough-shaped gripping lug at the inner edge portion.

8. A medical sieve basket assembly comprising:
   a handle comprising:
      a base body having or forming a handle bar and a holding portion adjoining the handle bar; and
      at least one fixing lug that is eyelet-shaped or bent and is arranged at an end of the holding portion opposite the handle bar for pivotal mounting of the handle,
      the base body comprising a planar sheet metal, which, at the end of the holding portion opposite the handle bar, is made as one piece into at least one lug-like projection extending the holding portion in a direction opposite the handle bar, the at least one lug-like projection being bent with respect to the holding portion to form the at least one fixing lug such that the at least one fixing lug is configured over its width for pivotal mounting of the handle; and
   a lid comprising at least one fixing strut or at least one hinge pin that is circumferentially enclosed by the at least one fixing lug and to which the handle is pivotably attached.

9. The lid according to claim 8, wherein in a rest position of the handle, in which the handle rests with the base body against the lid, the at least one fixing lug is positioned on a side of the handle facing the lid.

10. The lid according to claim 9, wherein:
    at least one channel-shaped or trough-shaped gripping lug is formed on an inner edge portion of the handle bar; and
    the lid comprises a recess or trough positioned and provided and adapted such that the gripping lug is recessed into the recess or trough in the rest position of the handle.

11. The lid according to claim 9, wherein a side of the lid facing the handle in the rest position of the handle is an upper lid side, and the fixing strut does not project beyond the upper lid side.

12. The lid according to claim 11, wherein a deflection of the handle relative to the lid is limited to a maximum deflection angle of 80° to 89°.

13. The lid according to claim 12, wherein a relative position between a lower edge of the holding portion facing the lid and the at least one fixing lug is determined in such a way that, when the maximum deflection angle is reached, the lower edge abuts on the upper lid side.

14. A method of forming a handle for a lid from a sheet-metal blank, the handle comprising: a base body having or forming a handle bar and a holding portion adjoining the handle bar, and at least one fixing lug that is eyelet-shaped or bent and is arranged at an end of the holding portion opposite the handle bar for pivotal mounting of the handle, wherein the base body comprises a planar sheet metal, which, at the end of the holding portion opposite the handle bar, is made as one piece into at least one lug-like projection extending the holding portion in a direction opposite the handle bar, the at least one lug-like projection being bent with respect to the holding portion to form the at least one fixing lug such that the at least one fixing lug is configured over its width for pivotal mounting of the handle, the method comprising the steps of:
   forming the at least one lug-like projection into the at least one fixing lug, the at least one fixing lug being curved such that the at least one fixing lug takes on an open, bent shape;
   inserting a fixing strut of the lid into the at least one fixing lug so that the at least one fixing lug encloses the fixing strut; and
   forming the at least one fixing lug in such a way that a free end of the at least one fixing lug is arranged closer to the base body and/or the free end comes to rest on the base body and the fixing strut is enclosed and pivotably secured by the at least one fixing lug.

15. The method according to claim 14, wherein, at an inner edge of the handle bar, the sheet-metal blank further is shaped into at least one sheet-metal band widening the sheet-metal blank towards the at least one lug-like projection, and the method further comprises the step of:
   forming the sheet-metal band so that the sheet-metal band is a bent channel-shaped or trough-shaped gripping lug formed on an inner edge portion of the handle bar.

* * * * *